(12) United States Patent
Dai

(10) Patent No.: US 10,982,182 B2
(45) Date of Patent: *Apr. 20, 2021

(54) FLOW ELECTROPORATION DEVICE

(71) Applicant: Etta Biotech Co., Ltd., Suzhou (CN)

(72) Inventor: Edward Dai, Suzhou (CN)

(73) Assignee: ETTA BIOTECH CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/906,054

(22) Filed: Jun. 19, 2020

(65) Prior Publication Data
US 2020/0318056 A1 Oct. 8, 2020

Related U.S. Application Data

(63) Continuation of application No. 15/035,694, filed as application No. PCT/CN2014/090821 on Nov. 11, 2014, now Pat. No. 10,731,120.

(30) Foreign Application Priority Data

Nov. 11, 2013 (CN) .......................... 201310554226.1

(51) Int. Cl.
*C12M 1/42* (2006.01)
(52) U.S. Cl.
CPC .................... *C12M 35/02* (2013.01)
(58) Field of Classification Search
CPC ............. A61K 9/5068; A61K 48/0091; A61N 1/0412; A61N 1/327; C12N 15/87;
(Continued)

(56) References Cited

U.S. PATENT DOCUMENTS

| 4,107,024 A | 8/1978 | Fukuzuka |
| 4,165,273 A | 8/1979 | Azarov |
| 5,720,921 A | 2/1998 | Meserol |
| 5,873,849 A | 2/1999 | Bernard |

(Continued)

FOREIGN PATENT DOCUMENTS

| CN | 101426929 A | 5/2009 |
| CN | 103275874 A | 9/2013 |

(Continued)

OTHER PUBLICATIONS

Non-Final Office Action dated Mar. 8, 2018 for U.S. Appl. No. 15/035,694.

(Continued)

*Primary Examiner* — William H. Beisner
*Assistant Examiner* — Danielle B Henkel
(74) *Attorney, Agent, or Firm* — Schmeiser, Olsen & Watts, LLP

(57) ABSTRACT

The present invention discloses a flow electroporation device comprising a three-dimensional electrode device and a flow electroporation chamber, the three-dimensional electrode device comprising an electrode array and an electrode fixing assembly for fixing electrodes in the electrode array, the flow electroporation chamber comprising a cavity, an inlet, an outlet and an opening, the inlet, the outlet and the opening on the cavity, and the electrode array being inserted into the cavity through the opening. By means of the above-mentioned manner, the flow electroporation device of the present invention can achieve a high throughput cell treatment, and also can work under a low voltage condition, can avoid damages to cells brought by liquid flow, can reduce effects brought by heat and cathode effect induced by electric pulses, and can maintain an closed aseptic environment.

7 Claims, 4 Drawing Sheets

(58) Field of Classification Search
CPC ... C12N 2740/10051; C12N 2840/203; C12M 35/02
See application file for complete search history.

(56) References Cited

U.S. PATENT DOCUMENTS

| | | | |
|---|---|---|---|
| 6,241,701 | B1 | 6/2001 | Hofmann |
| 10,731,120 | B2 * | 8/2020 | Dai .................. C12M 35/02 |
| 2003/0073238 | A1 | 4/2003 | Dzekunov |
| 2004/0016745 | A1 | 1/2004 | Sun et al. |
| 2004/0167458 | A1 | 8/2004 | Draghia-Akli |
| 2005/0043726 | A1 | 2/2005 | McHale |
| 2006/0089674 | A1 | 4/2006 | Walters |
| 2008/0058706 | A1 | 3/2008 | Zhang |
| 2009/0053813 | A1 | 2/2009 | Evans |
| 2014/0121728 | A1 | 5/2014 | Dhillon |
| 2017/0080221 | A1 | 3/2017 | Dai |

FOREIGN PATENT DOCUMENTS

| | | | |
|---|---|---|---|
| CN | 103555574 | A | 2/2014 |
| CN | 103861202 | A | 6/2014 |

OTHER PUBLICATIONS

Final Office Action dated Oct. 5, 2019 for U.S. Appl. No. 15/035,694.
Non-Final Office Action dated Apr. 5, 2019 for U.S. Appl. No. 15/035,694.
Final Office Action dated Oct. 21, 2019 for for U.S. Appl. No. 15/035,694.
Advisory Action dated Mar. 2, 2020 for U.S. Appl. No. 15/035,694.
Notice of Allowance dated Apr. 9, 2020 for U.S. Appl. No. 15/035,694.
Zheng, Jiabo, "The Theoretical and Experimental Study on Sterilization Effect of High Voltage Pulse", China Master's Theses Full-Text Database, No. 03, Mar. 15, 2013, p. 32, para 2, p. 33, section 4.2.1, para 5, and section 4.2.2 and p. 34, and fig 4.1 {see ISR).
International Search Report dated Jan. 21, 2015 for PCT/CN2014/090821.
Written Opinion dated Jan. 21, 2015 for PCT/CN2014/090821.
International Preliminary Report on Patentability dated May 17, 2016 for PCT/CN2014/090821.

* cited by examiner

FLOW ELECTROPORATION DEVICE

CROSS-REFERENCE TO RELATED APPLICATIONS

This application is a continuation application of U.S. application Ser. No. 15/035,694, which is now U.S. Pat. No. 10,731,120, filed May 10, 2016, and entitled "FLOW ELECTROPORATION DEVICE," which claims priority to PCT Application No. PCT/CN2014/090821, having a filing date of Nov. 11, 2014, which is based upon and claims priority to CN Application No. 201310554226.1, having a filing date of Nov. 11, 2013, the entire contents of all priority documents are incorporated herein by reference.

TECHNICAL FIELD

The present invention relates to a device used for cell electroporation, in particular, to a flow electroporation device.

BACKGROUND TECHNOLOGY

Since early 1970s, the electroporation has been used to insert molecules into animal cells or plant cells. It is proved by researchers that when a cell is exposed to an instantaneous high-voltage pulse electric field, the cell membrane permeability increases due to a local fracture of cell membrane caused by the high voltage electric field such that pathways will be formed through the cell membrane, these pathways being referred as "electropore". Although the existing times of these pathways are brief, it is enough to satisfy the requirement of the macromolecules such as proteins or plasmid DNAs entering or outleting. The cell may tolerate the high voltage which is used to format these pathways, however, the cell may be killed when these pathways are formed if the voltage of the high-voltage pulse is too high, the lasting time of the electric field is too long, or the times of the high-voltage pulse electric field is too many.

At the earlier, the electroporation is carried out by using two parallel-plate electrodes fixed on two inside walls of a container respectively. The cell suspension prepared for electroporation and the molecules which are expected to be introduced into the cell are mixed, and the solution is added into the electroporation container and placed between the two electrodes. In order to improve the effect of cell electroporation, an instantaneous high-voltage pulse is applied to the electrodes by one or more times so as to apply a high-voltage electric field pulse on the cell suspension between the electrodes. However, the distance between the parallel-plate electrodes is large, the required voltage is usually up to several hundred or even several thousand of volts, causing security and reliability issues, and the generation of a cathode effect is unavoidable, which has a huge damage to the cells. The planar electrode arose later reduces the distance between electrodes, and can generate an equal electric field intensity under a lower voltage and brings well electroporation effects, but it deals with a small amount of cells every time and is completely not suitable for high throughput experiment operations.

There is an electroporation instrument employing a three-dimensional electrodes on the market, but it usually uses for electroporations in clinic such as for tumour tissues or living tissues, etc. This type of instruments has a small number of electrodes and a simple combination, and some of them even use two needle-like electrodes as the three-dimensional electrodes, which meet the requirement of a living body and is easy to penetrate into the tissue and the living body, however, it's hard to be used for experiment operations of electroporation on extracorporeal cells such as suspended cells or attached cells.

At the current market, the most common electroporation container has a small volume, and needs multiple times of repeated operations during electroporation. Although this repetition of adding samples into the container for electroporation is easy and convenient, this container only can satisfy the requirement of a small scale cell electroporation for researchers and is not suitable for high throughput cell electroporations. In this method, it is impossible to keep sterile and it can not meet the requirement of a large volume of cell electroporation, and adding samples repeatedly will lengthen the actual operation time. Those issues are adverse to the accomplishment of the experiment.

In 1980s, researchers started to research the flow electroporation experiment methods used in treating the large volume of cells. Generally, the flow electroporation employs adapted parallel-plate electrodes and the cell suspension required to conduct electroporation flows continuously and steadily through between the two electrodes until the entire cell suspension is carried through electroporation such that the electroporation for a large volume of cells is achieved. When the cell suspension steadily flows through the two electrodes, the cells will be exposed to a high electric field pulse which is provided continuously at a constant interval. The flow electroporation method comprises an electroporation chamber with openings for the electrodes and cell suspension in and out. However, according to the hydrodynamics laws, when the fluid flows through the pathway between the parallel plates, the fluid in the middle of the pathway and the fluid at the periphery of the pathway have a difference in the flow speed, and the flow speed of the fluid in the middle of the pathway is greater than the flow speed of the fluid at the periphery of the pathway; the smaller the size of the pathway is, the faster the flow speed is and the more obvious this effect is. This kind of effect of fluid will introduce a shear force which may cause damages to the cells and goes against to the experimental process of electroporation. For the throughput of experiment, it is desired that the volume between the parallel plates is the larger the better, which may be achieved by enlarging the distance between the electrodes; for the applied voltage, it is desired that the distance between the parallel plates is the smaller the better, which may be achieved by reducing the pulse voltage and decreasing the cathode effect; for hydrodynamics laws, it is desired that the distance between the parallel plates is not so small, and the shear force is required to be reduced to a small level which is small enough to have no damage to the cells. Therefore, although using the parallel plates to design a flow electroporation chamber is relatively simple, there are many limits.

SUMMARY

The present invention mainly provides a flow electroporation device which has a simple structure and is easy to process and manufacture.

To slove the above-mentioned problems, one technical scheme employed by the present invention is to provide a flow electroporation device comprising a three-dimensional electrode device and a flow electroporation chamber, the three-dimensional electrode device comprising an electrode array and an electrode fixing assembly, electrodes forming the electrode array being fixed to the electrode fixing assembly, the flow electroporation chamber comprising a cavity, an inlet, an outlet and an opening, the inlet, the outlet and the opening being communicated with the cavity, and the electrode array being inserted into the cavity through the opening.

In a preferable embodiment of the present invention, the electrode array comprises a plurality of electrodes, and each electrode has a slender structure of electrical conductive material.

In a preferable embodiment of the present invention, the plurality of electrodes in the electrode array is arranged according to an equilateral polygon, and the distances between every two adjacent electrodes in the electrode array are equal.

In a preferable embodiment of the present invention, a shape of the electrode array is an equilateral hexagon formed by several equilateral triangles, and the electrodes are located at the vertexes of the equilateral triangles, respectively.

In a preferable embodiment of the present invention, the cross section of the cavity is circular or polygonal in shape.

In a preferable embodiment of the present invention, the flow electroporation device further comprises a drainage assembly which is communicated with the inlet or the outlet. The drainage assembly is selected from the group consisting of a peristaltic pump, a rotary pump, a piston, a diaphragm pump, or a gearing transmission device.

The beneficial effects of the present invention are as follow: the flow electroporation device of the present invention can achieve a high throughput cell treatment, and also can work under a low voltage condition, can avoid damages to cells brought by liquid flow, can reduce effects brought by heat and cathode effect induced by electric pulses, can maintain an enclosed aseptic environment, and can ensure that most of the cell suspension has been applied the field pulse for an optimal times.

BRIEF DESCRIPTION OF DRAWINGS

For clearly explaining the technical schemes in the embodiments of the present invention, the accompanying drawings used in describing the embodiments are briefly introduced in the following, and apparently, the following described drawings are merely a part of the embodiments of the present invention, and other drawings can be obtained according to these drawings by one of ordinary skill in the art without creative work, wherein.

Figure 1:
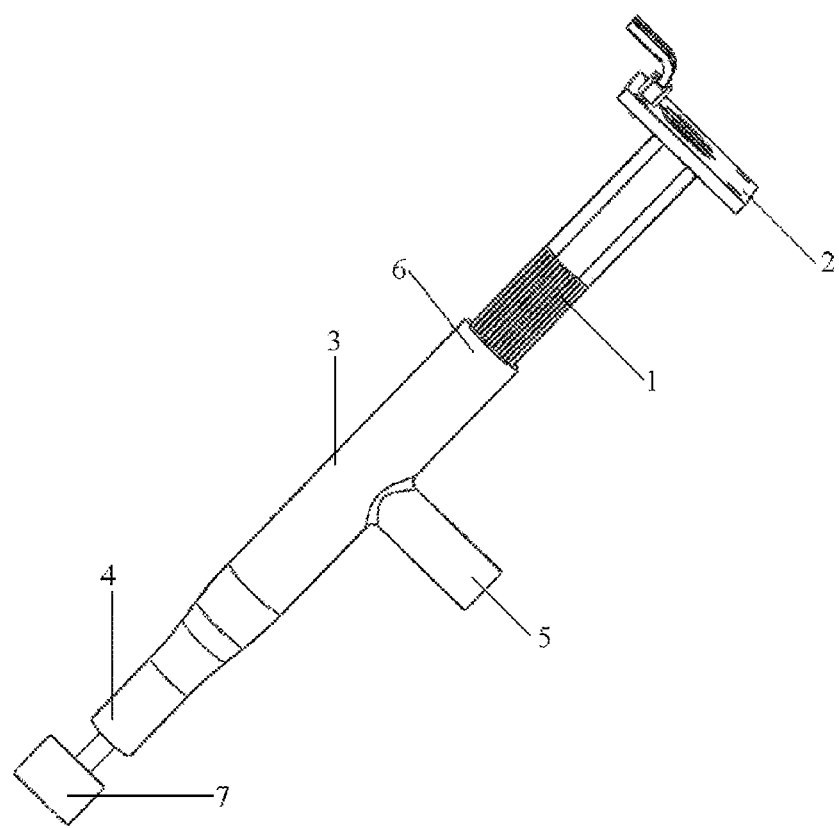
FIG. 1 is a structure schematic diagram of a preferable embodiment of a flow electroporation device of the present invention.

The drawing reference signs of the parts are as follow:
1—electrode array, 2—electrode fixing assembly, 3—cavity, 4—inlet, 5—outlet, 6—opening, 7—drainage assembly, 8—first interface, 9—second interface.

DETAILED DESCRIPTION OF EMBODIMENTS

In the following, the technical schemes in the embodiments of the present invention are explained clearly and fully, and apparently, the described embodiments are merely a part of the embodiments of the present invention, not all of the embodiments. Based on the embodiments of the present invention, all other embodiments obtained by one of ordinary skill in the art without creative work belong to the scope protected by the present invention.

Embodiment 1

Referring to FIG. 1, a flow electroporation device is provided, which comprises a three-dimensional electrode device and a flow electroporation chamber, the three-dimensional electrode device comprising an electrode array 1 and an electrode fixing assembly 2, and the electrode array 1 being fixed on the electrode fixing assembly 2.

The flow electroporation chamber employs a circular tubular container comprising a cavity 3, an inlet 4, an outlet 5, an opening 6 and a drainage assembly 7, the inlet 4 and the outlet 5 can be more than one, and the fluid flows in through at least one of the inlet 4 and flows out through at least one of the outlet 5 when in use. In this embodiment, the inlet 4 and the outlet 5 both are one, and the inlet is at the bottom of the cavity 3, the outlet 5 is at the side of the cavity 3, and the opening 6 is at the top of the cavity 3. The electrode array 1 is inserted into the cavity 3 through the opening 6. The flow electroporation chamber may be made of a glass tube, and also may be made of other biocompatible organic materials; and the size of the container may be adjusted according to the shape of the electrode array.

The drainage assembly 7 may be positioned at the inlet 4, and also may be located at the outlet 5, and in this embodiment, the drainage assembly 7 is communicated with the inlet 4. The drainage assembly 7 may be a peristaltic pump, a rotary pump, a piston, a diaphragm pump, or a gearing transmission device. When the flow electroporation device works, the drainage assembly 7 introduces the fluid into the flow electroporation chamber, and meanwhile, the electrode array 1 is applied with an electric pulse to work.

Figure 2:
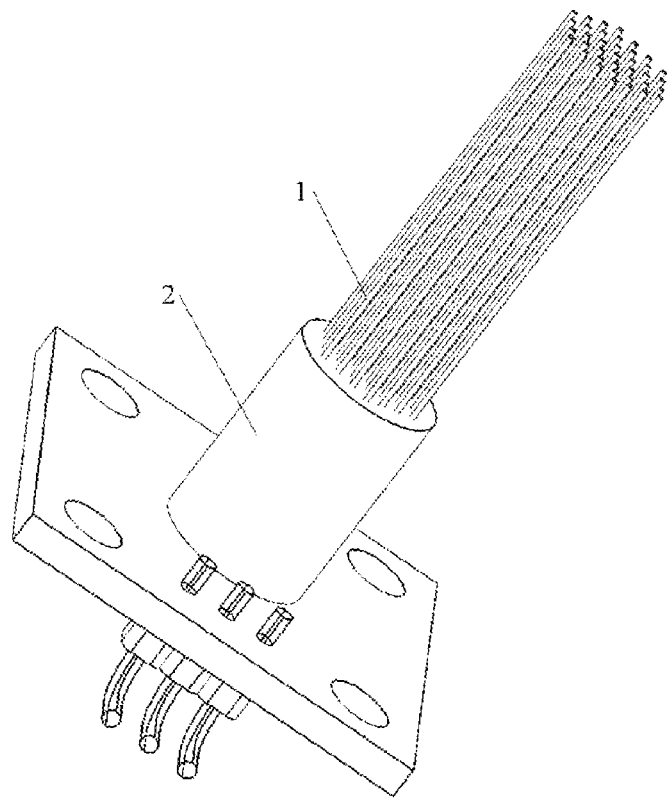
FIG. 2 is a structure schematic diagram of the three-dimensional electrode array in the flow electroporation device of FIG. 1.

Referring to FIG. 2, the electrode array 1 is formed by arranging cylindrical electrodes according to certain rules, these electrodes may be made of stainless steel, and also may be made of other electric conductive material, and these electrodes may be solid, and also may be hollow. The electrode array 1 applies electric pulses on the cells to achieve electroporation for the cells via the electrical field generated between the electrodes. The overall arrangement of the electrodes in the electrode array 1 is in a regular hexagon formed by regular triangle units. The distance between the electrodes and the number of the electrodes may be adjusted within a certain range, and the distance between the electrodes ranges within 100 μm-10 mm, and the smaller the distance is, the lower the required electroporation voltage is. The adjustment principle for the number of the electrodes is that after adjusted, the electrode array is still a regular hexagon formed by a plurality of regular triangle units. The electrode may be in any shape such as cylindrical shape, and the diameter thereof ranges from 0.01 mm to 2 mm. The electrode fixing assembly 2 mainly is used for fixing the position of the electrodes to maintain the electrode array in a regular arrangement, and is made of a biocompatible material, wherein one preferable material is polydimethylsiloxane (PDMS).

The material of the electrode influences the process difficulty, the manufacturing cost and the biocompatibility, etc. of the device. Most of the metal electrodes such as a copper or aluminium electrode have a bad biocompatibility, and some of the metal electrodes such as a gold or silver electrode have a very expensive cost, and it is found after a long-term experimental research that the stainless steel is an excellent material for the three-dimensional electrode. The stainless steel possesses a good biocompatibility, and meanwhile is easy to be processed to form a relatively long electrode which can be able to be mass produced, and is very suitable to serve as the electrode material of the electrode array 1. Both too large and too small diameter of the stainless steel electrode may bring adverse effects to the device. When the diameters are too large, the effective area of the electroporation may be reduced, resulting in a decrease on the number of cells dealt with by electroporation, and going against high throughput of cell electroporation. When the diameters are too small, the electrodes are easily bended resulting in a large increase of the manufacturing cost. The stain steel material also possesses characteristics such as easy to clean and difficult to be oxidized, and these characteristics enable it to be reused for multiple times without affecting the conduction properties thereof.

Figure 3:
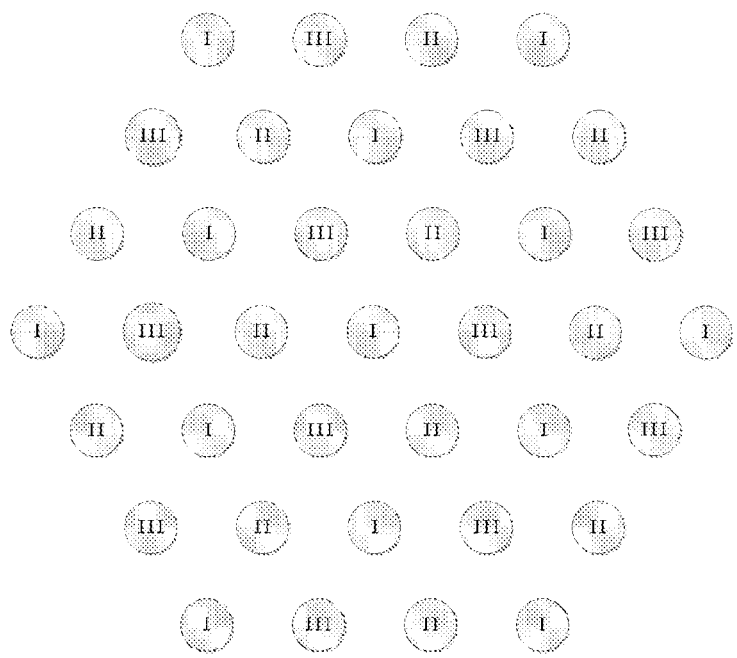
FIG. 3 is a schematic diagram of the electrode connection regulation of the three-dimensional electrode array in the flow electroporation device of FIG. 1.

FIG. 3 is a schematic diagram of the electrode connection of the electrode array 1, the number of the electrodes forming the electrode array may be adjusted within a certain range, and both the electrode distance and the size of the periphery shape may be vary according to the requirement of embodiments. The adjustment principle for the number of the electrodes is that after adjusted, the electrode array is still a regular hexagon formed by a plurality of regular triangle units. In FIG. 3, the electrode array formed by 37 electrodes is divided into three groups which are represented by Group I, Group II and Group III, respectively, and in the electrode array, each three electrodes neighboring each other has electrodes numbered as I, II and III, and the electrodes which belong to the same group will be connected together.

Figure 4:
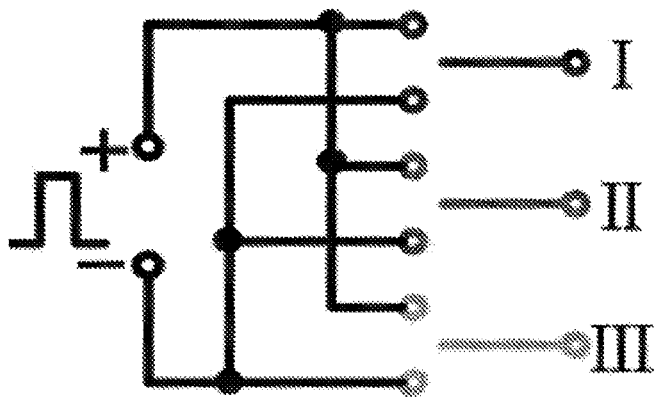
FIG. 4 is a schematic diagram of the power-on manner of the three-dimensional electrode array in the flow electroporation device of FIG. 1.
Figure 5:
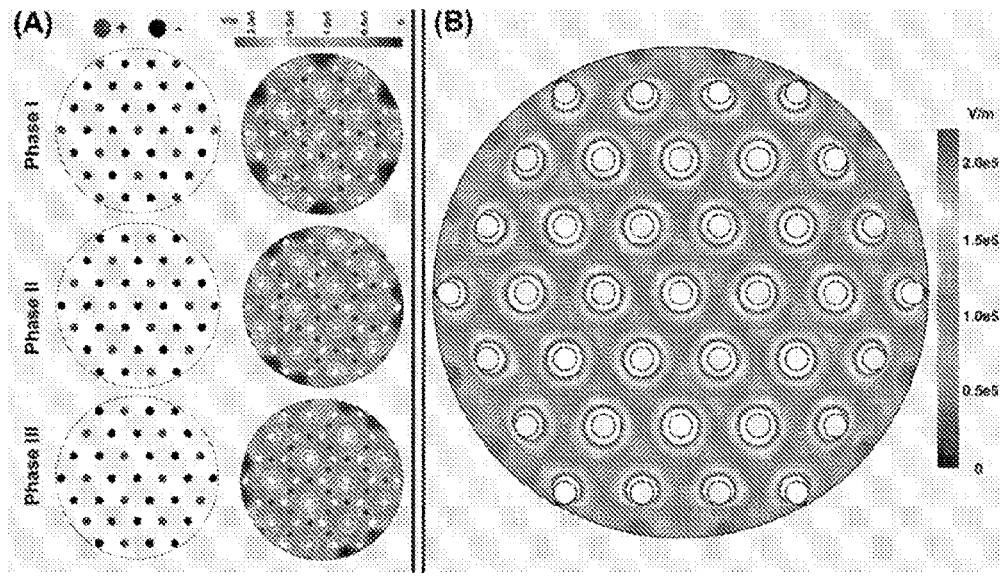
FIG. 5 is a schematic diagram of the electric field distribution of the three-dimensional electrode device in the flow electroporation device of FIG. 1.

FIG. 4 is a schematic diagram of a typical power-on manner of the electrode array 1, the input of the electrode array has three electrical interfaces represented by Interface (I), Interface (II) and Interface (III) respectively, the three interfaces are connected with the electric voltage pulse via switches, wherein the preferable implementation manner of the switches is a relay or an optical-coupled switch controlled by a digital signal, and the electric voltage pulse is provided by an electroporation instrument, a pulse generator or a bio-stimulator. The connection manner of the three switches is not limited to one type, and may be adjusted according to a specific embodiment, for example, one of them connects with the positive pole and the other two of them connect with the negative pole. In a preferred embodiment, three successive voltage pulses are classified as one group, and these three voltage pulses are named as t1, t2 and t3, or named as phase I, phase II and phase III; when the voltage pulse is t1 or phase I, Interface (I) connects the positive pole, and the Interfaces (II) and (III) connect the negative pole; when the voltage pulse is t2 or phase II, Interface (II) connects the positive pole, and the Interfaces (I) and (III) connect the negative pole; when the voltage pulse is t3 or phase III, Interface (III) connects the positive pole, and the Interfaces (I) and (II) connect the negative pole; the number of the voltage pulses applied during electroporation is not limited to 3, and for obtaining an uniform treatment, the number generally is a multiple of 3. Corresponding to this preferred embodiment, the simulated distribution of the electric field when the electrode network is applied with the voltage pulse is shown in FIG. 5, FIG. 5(A) is the corresponding simulated distributions of the electric fields at the three successive voltage pulses, respectively; FIG. 5(B) is an effect diagram of a superposition of the simulated distributions of the electric fields after the three successive voltage pulses, wherein in the simulated conditions, the electrode distance is 7500 µm, the size of the electrodes is 300 µm, and the number of the electrode is 37.

Embodiment 2

Figure 6:
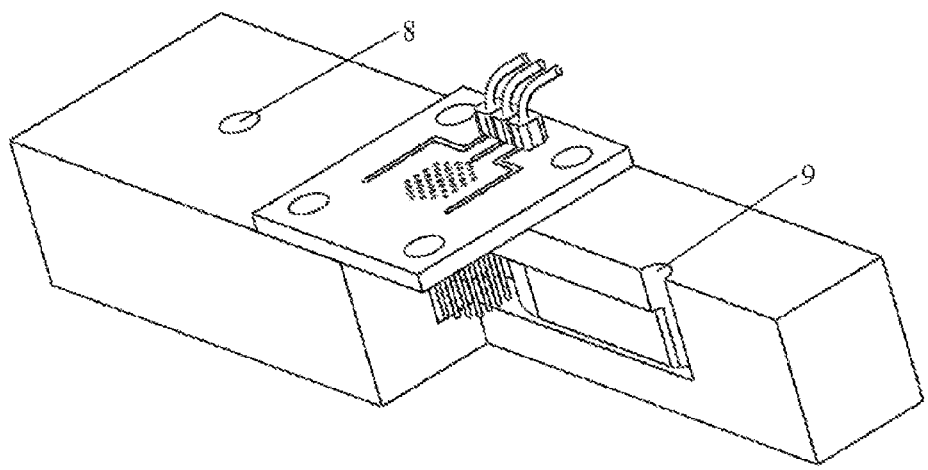
FIG. 6 is a structure schematic diagram of another preferable embodiment of a flow electroporation device of the present invention.

Referring to FIG. 6, this embodiment is similar to Embodiment 1 by differing in that the flow electroporation chamber is a cuboid container, and a first interface 8 and a second interface 9 are on the flow electroporation chamber and both can be used as a sample outlet and a sample inlet.

It is confirmed by researchers that, the forming conditions of electrodes relates to the cell type, the molecular type desired to introduce into the cell, or the molecular type desired to flow out from the cell. For any specific type of cells, there is an optimal treatment condition referred as a condition interval, specifically, a more specific condition within this condition interval can be chosen to conduct experiment. This condition interval is involved with the voltage strength, more specifically, with the electric field strength applied on the cells, the pulse duration, the pulse number and the pulse interval. In the flow electroporation device, the cell suspension flows through the flow electroporation chamber at a constant speed, and so the pulse interval and the speed of the suspension restrict each other, which is related to the optical pulse number of the cells. For the fluid within the container, the flow speed at the center region is greater than the flow speed close to the wall of the container, it is certain to cause that the pulse number applied on the cells flowing through the center region is smaller than a desired value, and the pulse number applied on the cells flowing closely to the chamber wall is greater than the desired value. In this way, it can give out an approximate relation expression, the ratio of the volume through the center region of the fluid to the total volume through the container is p=Vin/Vall, wherein, Vin is the volume of the cell suspension through the center region of the container, Vall is the total volume of the cell suspension through the container, and p is the ratio of the above two volumes.

When determining the pulse interval and the suspension flow speed, the volume parameter usually employed is the total volume through the container; it can be seen that, the greater the parameter p is, the more beneficial to the cell suspension through the center region of the container, specifically, the greater the parameter p is, the closer the pulse number applied on the cell suspension flowing through the center region of the container is to the desired value, while the volume flowing closely to the chamber wall occupies a very small percentage in the total volume, and the cells of this volume is applied a number of pulses smaller than the desired value, but the effect brought by it can be ignored.

The variable flow electroporation experiment on cells was conducted by utilizing the flow electroporation device. HEK-293A cells were selected and used to conduct the flow electroporation, and GFP plasmids were used as the marker in the experiment. If the cell experiences the electroporation, GFP plasmid will get into the cell and express green fluorescent proteins within the cell, the green fluorescent proteins can present green fluorescence under a fluorescence microscope. Therefore, the electroporation rate of the cells can be obtained by dividing the total cell number by the cell number in the fluorescence field. From another perspective, the greater the fluorescence intensity at the same cell density is, the higher the electroporation efficiency is.

When conducting the experiment, a sample containing HEK-293A cells and GFP plasmids was injected into the electroporation chamber, and the sample flowed at a specified constant speed, and meanwhile power-on pulse conducted electroporation on the sample; the untreated sample flowed into the electroporation chamber, and at the same time the treated sample was discharged. The treated sample discharged was collected and transferred into a culture plate, a culture medium was added in, and the sample was cultured for 24 hours and then observed under the fluorescence microscope.

Figure 7:
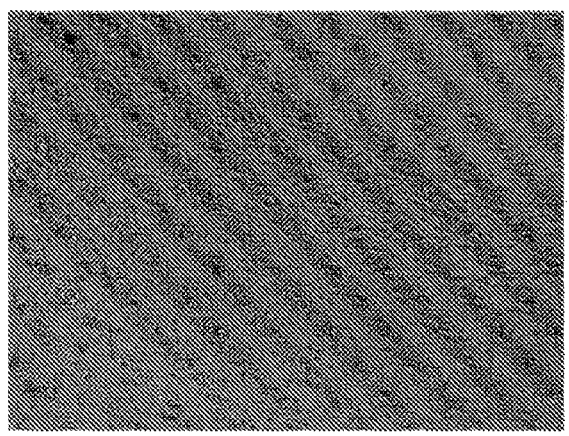
FIG. 7 is photos of HEK-293A cells at 24 hours post-electroporation under a fluorescence microscope in the present invention.
Figure 7:
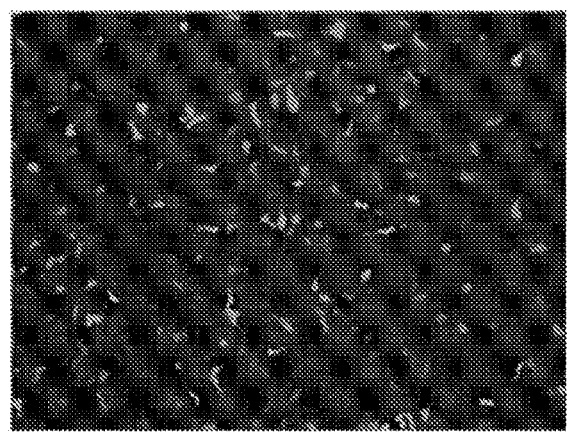
Figure 7:
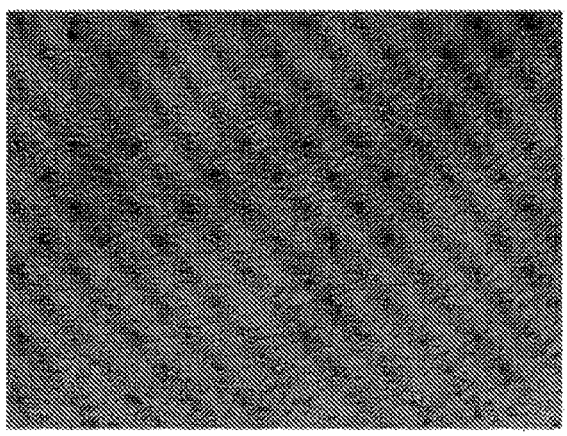
Figure 7:
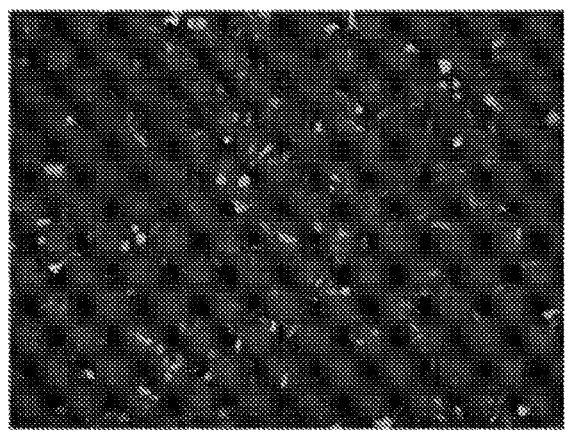

FIG. 7 is results of the bioexperiment by utilizing the device and describes the results of HEK-293A cells at 24 hours post-electroporation by photographing under the fluorescence microscope, the cells expressing the GFP plasmids which get into the cells due to the electroporaion, and giving out green light under the fluorescence microscope. In the two groups of photos of the electroporation experiment, a light field viewing of the cells representing the number of the cells undergoing electroporation are on the left, and a fluorescence field viewing of the cells reflecting the circumstance of the electroporaion are on the right.

The above are only embodiments of the present invention, and are no way to limit the scope of the present invention. Any equivalent structures or process changes, or direct or indirect application on other relative technical fields by taking advantage of the content of the present invention should be covered by the scope of the present invention.

What is claimed is:

1. A flow electroporation device comprising:
   a flow electroporation chamber having a body section and a hollow internal cavity;
   a first interface integrated with the body section, the first interface being a sample inlet in fluid communication with the hollow internal cavity;
   a second interface integrated with the body section, the second interface being a sample outlet in fluid communication with the hollow internal cavity, wherein the hollow internal cavity extends between the first interface and the second interface within the flow electroporation chamber; and
   an electrode fixing assembly comprising an electrode array fixed thereto, the electrode fixing assembly slidably inserted into the hollow internal cavity through the body section of the flow electroporation chamber so that at least the electrode array resides within the hollow internal cavity, wherein the electrode fixing assembly and the electrode array are physically separate components from the flow electroporation chamber that do not form part of the body section of the flow electroporation chamber;
   wherein the electrode array comprises at least three electrodes fixed to the electrode fixing assembly, each electrode being immediately adjacent to at least two other electrodes, the at least three electrodes having an elongated shape and formed from an electrically conductive material;
   wherein the at least three electrodes having the elongated shape extend from the electrode fixing assembly proximate a top surface of the body section in a direction towards a bottom surface of the body section such that all sides of the at least three electrodes contact a fluid introduced into the flow electroporation chamber through the first interface while the fluid passes through the flow electroporation chamber and exits through the second interface;
   wherein the at least three electrodes are arranged according to an equilateral polygon with an equal distance between two adjacent electrodes in the electrode array, the equilateral polygon is an equilateral hexagon formed by several equilateral triangles, and the at least three electrodes are located at vertexes of the equilateral triangles, respectively;
   wherein the electrode array is divided into groups, at least one electrode of a first group is surrounded by electrodes of a second group, and electrodes belonging to a same group are connected together;
   wherein an input of the electrode array has electrical interfaces connected with electric voltage pulses via switches for applying an electric voltage pulse alternately, the switches being at least one of: relays or optical-coupled switches, controlled by a digital signal;
   wherein an electric pulse of a first polarity and an electric pulse of a second polarity are respectively applied on the groups of the electrode array in an alternating time period, an electric pulse of a same polarity is applied to the electrodes in the same group;
   wherein the electric pulse of the first polarity is applied to one of the groups and the electric pulse of the second polarity is applied to a remaining group, and the electrodes corresponding to the electric pulse of the second polarity are surrounded by the electrodes corresponding to the electric pulse of the first polarity, further wherein the first polarity and the second polarity are opposite.

2. The flow electroporation device according to claim 1, wherein a cross section of the body section is polygonal.

3. The flow electroporation device according to claim 1, further comprising a drainage assembly positioned at the first interface, the drainage assembly configured to introduce the fluid into the flow electroporation chamber via the first interface.

4. The flow electroporation device according to claim 3, wherein the drainage assembly is at least one of a peristaltic pump, a rotary pump, a piston, a diaphragm pump, and a gearing transmission device.

5. The flow electroporation device according to claim 1, wherein the flow electroporation chamber is made from at least one of a glass tube and a bio-compatible material.

6. The flow electroporation device according to claim 1, wherein the first interface and the second interface are disposed on a same wall of the body section.

7. The flow electroporation device according to claim 1, wherein the first interface and the second interface are coplanar.

* * * * *